United States Patent
Durrani

(10) Patent No.: US 8,083,773 B2
(45) Date of Patent: Dec. 27, 2011

(54) APPARATUS FOR MINIMALLY INVASIVE POSTERIOR CORRECTION OF SPINAL DEFORMITY

(75) Inventor: Muhammad Abubakar Atiq Durrani, Mason, OH (US)

(73) Assignee: Muhammad Abubakar Atiq Durrani, Mason, OH (US)

( * ) Notice: Subject to any disclaimer, the term of this patent is extended or adjusted under 35 U.S.C. 154(b) by 684 days.

(21) Appl. No.: 11/995,404

(22) PCT Filed: Jul. 14, 2006

(86) PCT No.: PCT/US2006/027554
§ 371 (c)(1),
(2), (4) Date: May 19, 2008

(87) PCT Pub. No.: WO2007/011815
PCT Pub. Date: Jan. 25, 2007

(65) Prior Publication Data
US 2010/0249844 A1 Sep. 30, 2010

Related U.S. Application Data

(60) Provisional application No. 60/699,676, filed on Jul. 15, 2005.

(51) Int. Cl.
*A61B 17/70* (2006.01)
(52) U.S. Cl. ........................................ 606/259; 606/264
(58) Field of Classification Search .................. 606/254, 606/261, 86 A, 190, 279, 259, 263, 257, 260, 606/264; 403/220, 223
See application file for complete search history.

(56) References Cited

U.S. PATENT DOCUMENTS

| | | | | |
|---|---|---|---|---|
| 4,378,712 A | * | 4/1983 | Yoshifuji | 74/502.5 |
| 4,960,410 A | * | 10/1990 | Pinchuk | 604/96.01 |
| 5,649,926 A | * | 7/1997 | Howland | 606/279 |
| 5,672,175 A | * | 9/1997 | Martin | 606/86 A |
| 5,772,661 A | | 6/1998 | Michelson | |
| 6,193,721 B1 | | 2/2001 | Michelson | |
| 6,398,783 B1 | | 6/2002 | Michelson | |
| 6,447,546 B1 | * | 9/2002 | Bramlet et al. | 623/17.16 |
| 6,454,711 B1 | | 9/2002 | Haddad et al. | |
| 6,527,776 B1 | | 3/2003 | Michelson | |
| 6,620,163 B1 | | 9/2003 | Michelson | |
| 7,763,052 B2 | * | 7/2010 | Jahng | 606/254 |
| 2005/0033291 A1 | | 2/2005 | Ebara | |
| 2005/0080418 A1 | | 4/2005 | Simonson et al. | |
| 2005/0124991 A1 | | 6/2005 | Jahng | |

OTHER PUBLICATIONS

International Search Report, dated Feb. 16, 2007, for PCT Application No. PCT/US2006/027554.
Written Opinion of the International Searching Authority, dated Feb. 16, 2007, for PCT Application No. PCT/US2006/027554.
(various authors); Research Report—Spinal Correction Device; Report No. 1286479; Jul. 5, 2005.
Screenshot from www.medtronicsofamordanek.com/health-disorders-scoliosis.html, dated Apr. 5, 2005.

* cited by examiner

*Primary Examiner* — Pedro Philogene
(74) *Attorney, Agent, or Firm* — Frost Brown Todd LLC

(57) ABSTRACT

An apparatus is operable to correct spinal deformities caused by scoliosis and the like. The apparatus may be used in a minimally invasive fashion and through the posterior side of the patient. A combination of internal screws and rods, as well as external pins, rods, and correction mechanisms, are used to obtain facet unlocking and translational correction of the affected vertebrae. The internal rods are inserted percutaneously and are secured to the affected vertebrae to maintain the deformity correction. External components are then removed, and the small incisions are sutured.

19 Claims, 13 Drawing Sheets

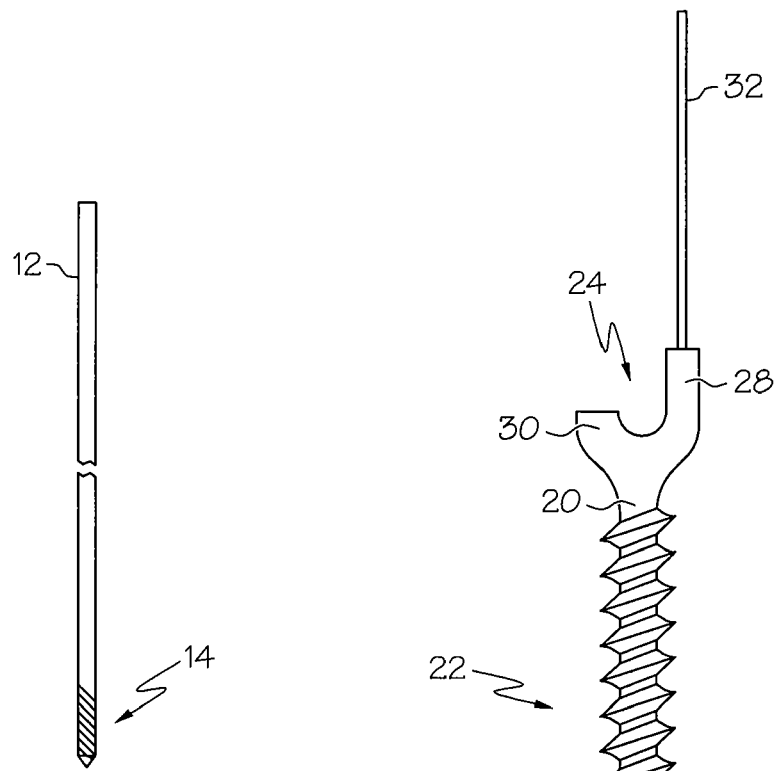
FIG. 1
FIG. 2
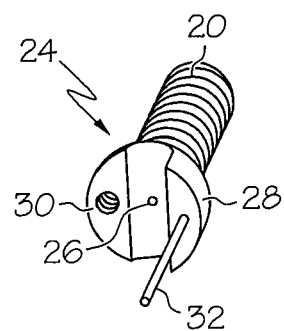
FIG. 3

APPARATUS FOR MINIMALLY INVASIVE POSTERIOR CORRECTION OF SPINAL DEFORMITY

PRIORITY

This application claims priority to and the benefit of PCT application PCT/US2006/027554, filed Jul. 14, 2006, which claims priority to U.S. Provisional Patent Application Ser. No. 60/699,676, filed Jul. 15, 2005, the disclosure of each of which is incorporated by reference herein.

BACKGROUND OF THE INVENTION

Spinal deformities are found in a variety of forms, such as lateral deformity associated with scoliosis and "round back" deformity associated with kyphosis. A variety of types of scoliosis are known, including but not limited to juvenile, adolescent, adult, idiopathic, congenital, degenerative, acquired, structural, and functional scoliosis. Similarly, a variety of types of kyphosis are known, including but not limited to postural, structural, Scheuermann's, congenital, Gibbus deformity, hyperkyphosis, mobile, and fixed kyphosis. Several methods and devices have been used and made to treat or correct such spinal deformities, but no one prior to the inventor has made or used the invention described in the appended claims.

BRIEF DESCRIPTION OF THE DRAWING

While the specification concludes with claims that particularly point out and distinctly claim the invention, it is believed the present invention will be better understood from the following description taken in conjunction with the accompanying drawings, in which like reference numerals identify the same elements. The drawings and detailed description which follow are intended to be merely illustrative and are not intended to limit the scope of the invention as set forth in the appended claims.

FIG. 1 depicts a threaded screw guide wire.
FIG. 2 depicts a cannulated screw.
FIG. 3 depicts a perspective end view of the cannulated screw of FIG. 2.

DETAILED DESCRIPTION OF THE INVENTION

Figure 4:
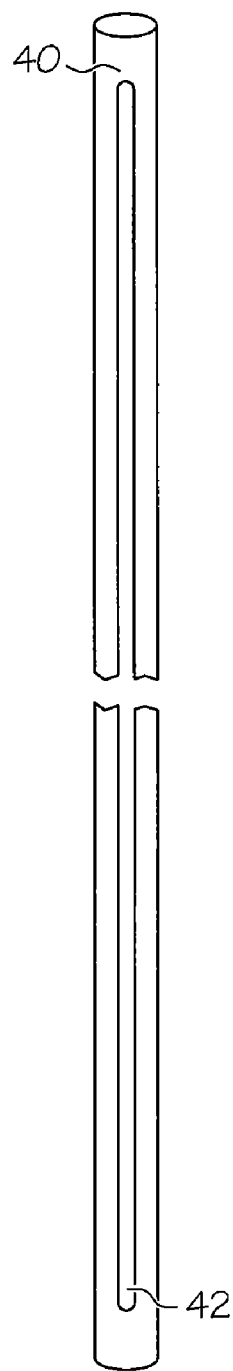
FIG. 4 depicts a slotted external rod.

The following description should not be used to limit the scope of the present invention. Other examples, features, aspects, embodiments, and advantages of the invention will become apparent to those skilled in the art from the following description, which includes by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive. It should therefore be understood that the inventor contemplates a variety of embodiments that are not explicitly disclosed herein.

The apparatus (10) of the present example comprises a plurality of screw guide wires (12), a plurality of cannulated screws (20), a plurality of external rods (40, 60), a plurality of facet unlocking mechanisms (80), a plurality of translational corrective mechanisms (100), a pair of rod guide wires (120), a pair of internal rods (130 or 150), and a plurality of clamping members (170).

As illustrated in FIG. 1, each of the screw guide wires (12) of the present example has a self-tapping threaded end (14). The self-tapping threaded end (14) is configured such that the screw guide wire (12) may be inserted into bone, such as a vertebra (202), with a screwing motion. The screw guide wires (12) of the present example each have a length that is substantial enough to provide protrusion of the screw guide wires (12) beyond the skin level after the screw guide wires (12) have been installed in an affected vertebrae (202), as will be discussed below.

As illustrated in FIGS. 2 and 3, each cannulated screw (20) of the present example comprises a threaded portion (22), a "U"-shaped proximal portion (24), and an opening (26) positioned along the axis of the cannulated screw (20). The opening (26) is dimensioned such that its inner diameter is greater than the outer diameter of a screw guide wire (12). The "U"-shaped proximal portion (24) comprises a first arm (28) and a second arm (30), which together define the "U" shape. Alternatively, the first and second arm (28, 30) may define a triangular, rectangular, or other shape. In any event, the "U"-shaped portion (24) of the present cannulated screw (20) is configured to accommodate an internal rod (130), as will be described below.

As shown, the first arm (28) is longer than the second arm (30). However, it will be appreciated that the first and second arms (28, 30) may have any other configuration. The first arm (28) has a leading post (32) projecting therefrom. The leading post (32) is parallel to the axis of the cannulated screw (20).

The leading post (32) is removable from the cannulated screw (20), such as by unscrewing the leading post (32). Structural and functional variations of the cannulated screw (20) and its components will be apparent to those of ordinary skill in the art. It will also be appreciated that a cannulated screw (20) may be substituted with any other suitable structure, including but not limited to other fasteners or anchors (e.g., staples, etc.).

Figure 5:
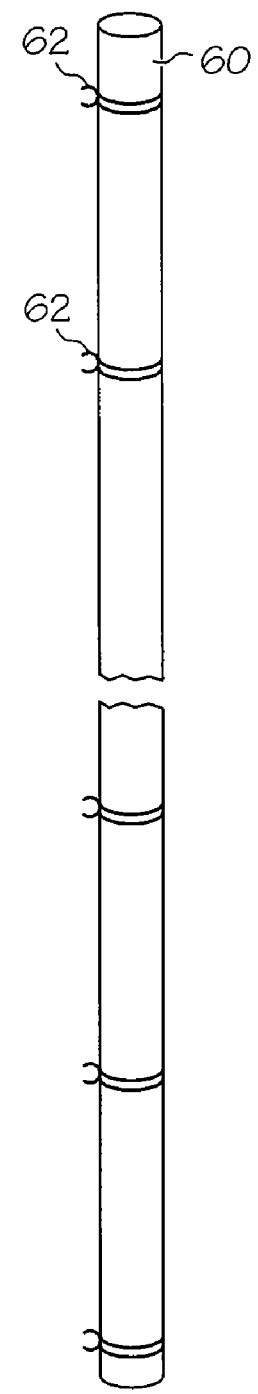
FIG. 5 depicts a clipping external rod.

As shown in FIGS. 4-5, external rods (40, 60) of the present example include a slotted external rod (40) and a clipping external rod (60). All of the external rods (40, 60) in the present example are substantially rigid, and have a length that exceeds the distance between the uppermost vertebra (202A) and lowermost vertebra (202B) of the affected vertebrae (202). Alternatively, any other suitable length may be used. As will be appreciated, rods (40, 60) of the present example are configured to provide stabilization for other components relative to affected vertebrae (202), though rods (40, 60) may serve a variety of alternative purposes.

The slotted external rod (40) has an elongate slot (42) extending along the axis of the slotted external rod. The elongate slot (42) is dimensioned to receive a leading post (32) of a cannulated screw (20), thereby permitting relative axial movement between the leading post (32) and the slotted external rod (40), but prohibiting relative translational movement between the leading post (32) and the slotted external rod (40). It will be appreciated that the elongate slot (42) may accommodate several leading posts (32) in alignment.

A variation of the slotted external rod (40) comprises a rod (not shown) having a plurality of clipping members, each of which extends from the side of the external rod. In this embodiment, the clipping members are configured to engage with leading posts (32) of cannulated screws (20), and are permitted to freely slide longitudinally along the external rod. Other alternatives for the slotted external rod will be apparent to those of ordinary skill in the art.

In the present example, each of the clipping external rods (60) has a plurality of clipping members (62). Each clipping member (62) is configured to engage with a leading post (32) of a cannulated screw (20). Each clipping member (62) is further configured to prohibit relative axial and translational movement between the leading post (32) and the clipping external rod (60). Similar to the slotted external rod (40), each clipping external rod (60) may engage with several leading posts (32) in alignment. In one embodiment, the position of each clipping member (62) along the axis of the clipping external rod (60) is fixed. In another embodiment, the configuration of the clipping external rod (60) permits axial adjustment of the clipping members (62), such that the position of each clipping member (62) along the axis of the clipping external rod (60) may be adjusted prior to being selectively fixed.

Other variations of each type of external rod (40, 60) will be apparent to those of ordinary skill in the art.

Figure 6:
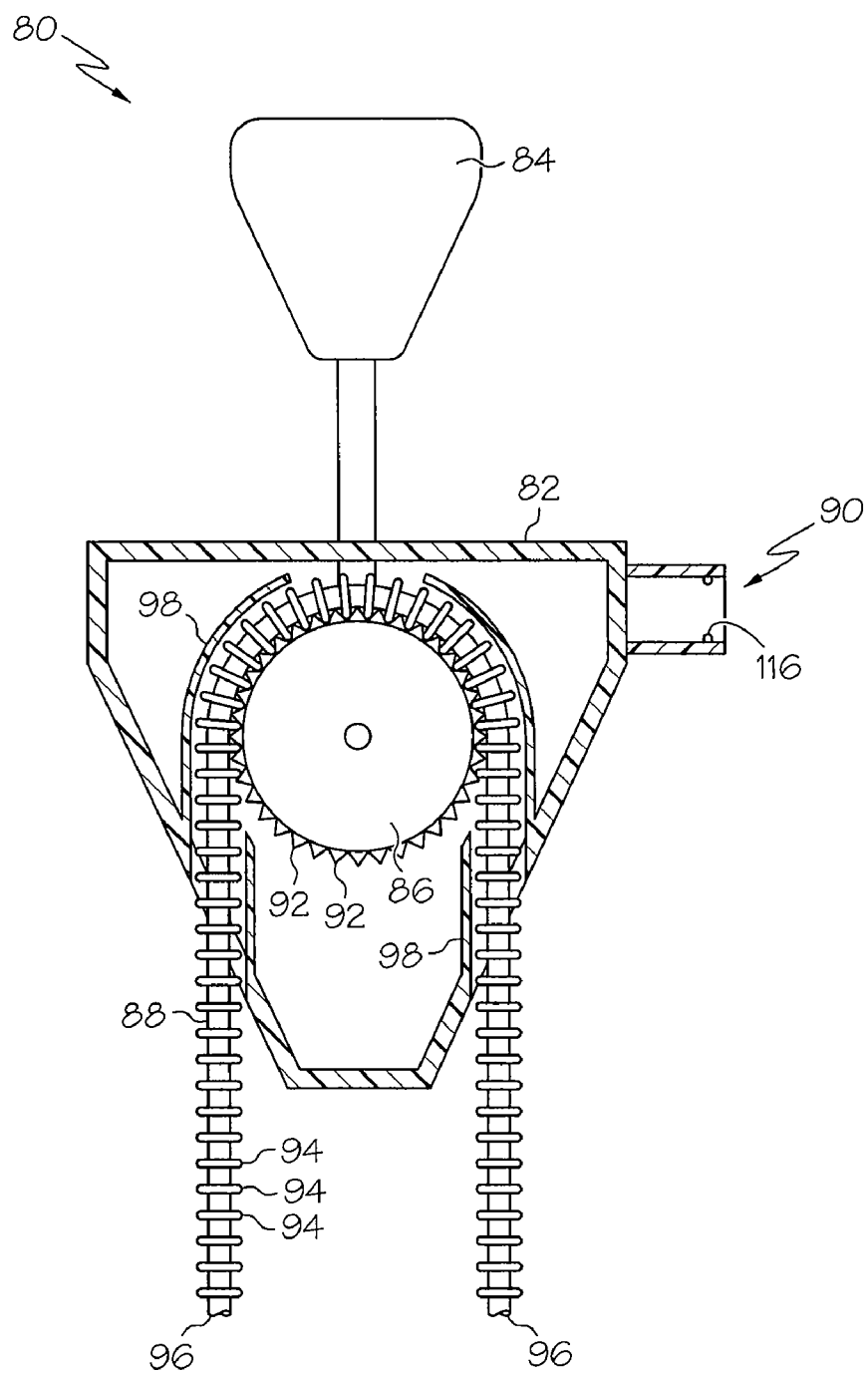
FIG. 6 depicts a cross-sectional view of a facet unlocking mechanism.

In the present example, and as shown in FIG. 6, each facet unlocking mechanism (80) comprises a housing (82), a knob (84), a pinion (86), and a flexible rack (88). The pinion is located within the housing, as is a portion of the flexible rack. The housing (82) further comprises a feature (90) configured to receive a translation screw (108) member of a translational corrective mechanism (100), which will be described below. The knob (84) and the pinion (86) are in mechanical communication (e.g., such as by bevel or screw gear, etc.), such that rotation of the knob (84) effects rotation of the pinion (86). Suitable configurations for providing such communication will be apparent to those of ordinary skill in the art. The pinion (86) comprises a plurality of teeth (92), which are configured to engage with ribs (94) on the flexible rack (88). This engagement between teeth (92) and ribs (94) causes flexible rack (88) to advance in response to rotation of pinion (86) (i.e. in the direction of the rotation of pinion (86)).

The flexible rack (88) has a pair of ends (96), and is configured such that it may flex to engage with the pinion (86). However, the flexible rack (88) is further configured such that it will resist flexion or buckling in response to axially-oriented forces acting upon the ends of the flexible rack (88). Each end (96) of the flexible rack (88) is configured to engage with a leading post (32) of a cannulated screw (20). Where each end (96) of the flexible rack (88) is engaged with a respective leading post (32), such engagement will permit the flexible rack (88) to transfer opposing axial forces to the leading posts (32) (e.g., "pushing" one leading post (32) while simultaneously "pulling" the other leading post (32)). Housing (82) of the present example further includes rails (98), which are configured to guide flexible rack (88). Of course, various alternative features may be used.

In another embodiment (not shown), a pair of rigid racks are used in place of a single flexible rack (88). In this embodiment, a rigid rack is positioned on each side of the pinion (86), such that one will "push" while the other "pulls" simultaneously upon rotation of the knob (84). The other features and functions of these rigid racks are similar to those of the flexible rack (88). In yet another embodiment, a portion of rack (88) is flexible (e.g., a portion within housing (82)), while another portion of rack (88) is rigid (e.g., a portion external to housing (82)).

In light of the foregoing, and as will be described in further detail below, the rotation of the knob (84) on a facet unlocking mechanism (80) is operable to effect the "pushing" of one leading post (32) while simultaneously effecting the "pulling" of another leading post (32), with the pushing and pulling varying with the direction in which the knob (84) is turned. Of course, there are a variety of other configurations for the facet unlocking mechanism (80) through which the same or similar results may be obtained. By way of example only, any suitable alternative to knob (84), pinion (86), flexible rack (88), or rigid racks may be used. Other alternative mechanisms and variations will be apparent to those of ordinary skill in the art.

Figure 7:
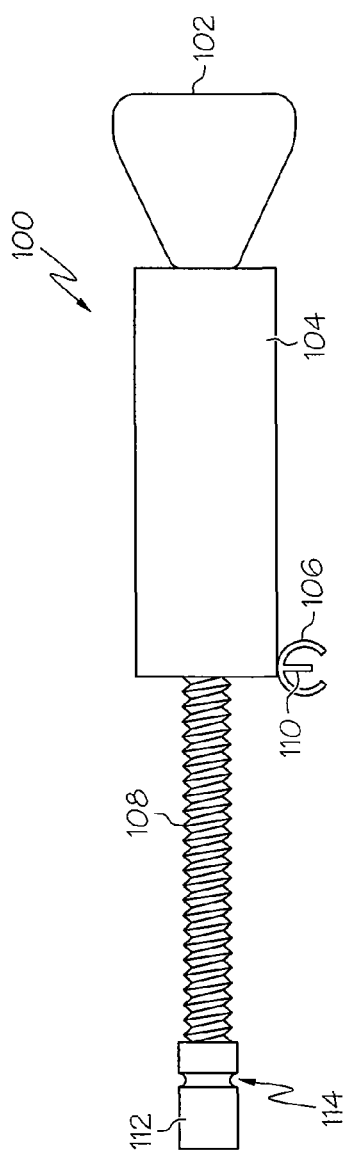
FIG. 7 depicts a translational corrective mechanism.

As shown in FIG. 7, each translation corrective mechanism (100) of the present example comprises a knob (102), a housing (104), a clip member (106), and a translation screw member (108). The knob (102) and the translation screw member (108) are in mechanical communication, and are configured such that rotation of the knob (102) will effect axial movement of the translation screw member (108). In other words, the translation screw member (108) is configured to advance and retract axially relative to the housing (104) in response to rotation of the knob (102). Suitable configurations for providing such a result will be apparent to those of ordinary skill in the art.

The clip member (106) for each translation corrective mechanism (100) is configured to engage with the slotted external rod (40). Thus, when a translation corrective mechanism (100) is so engaged with the slotted external rod (40), the clip member (106) prevents translational movement of the translation corrective mechanism (100) relative to the slotted external rod (40). The clip member (106) further comprises a pin (110), which protrudes radially outward relative to the housing (104) of the translation corrective mechanism (100). The pin (110) is configured to engage with the elongate slot (42) of the slotted external rod (40) when the translation corrective mechanism (40) is clipped to the slotted external rod (40). Thus, when a translation corrective mechanism (100) is so engaged with the slotted external rod (40), the pin (110) prevents rotation of the translation corrective mechanism (100) relative to the slotted external rod (40). Where the slotted external rod (40) is substituted with the external rod (60) having the freely longitudinally moving clip members (62), an aperture, recess, elongate slot, or other feature may be employed in such a rod (60) to accommodate the pin (110) of the clip member (106) for each translation corrective mechanism. Alternatively, pin (110) and/or clip members (62 or 106) may be configured such that pin (110) engages with a clip member (62). Still other suitable configurations will be apparent to those of ordinary skill in the art.

In one embodiment, the position of each clip member (106) along the axis of the housing (104) is fixed. In another embodiment, the configuration of the translation corrective mechanism (100) may permit axial adjustment of the clip members (106), such that the position of each clip member (106) along the axis of the housing (104) may be adjusted prior to being selectively fixed.

Figure 8:
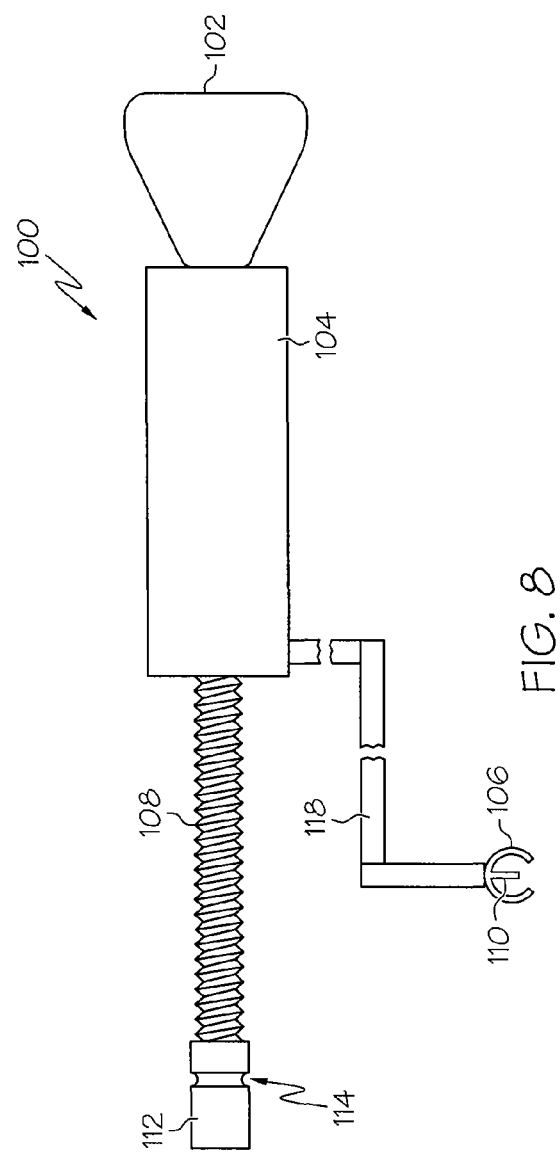
FIG. 8 depicts an alternate translation corrective mechanism.
Figure 9:
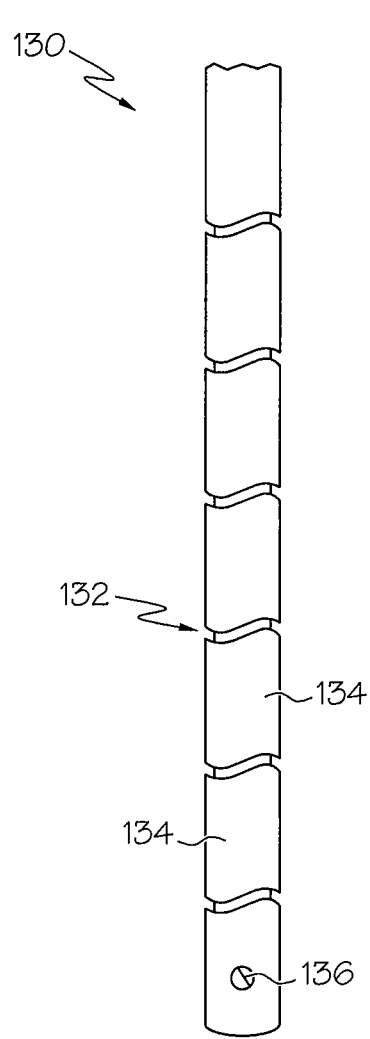
FIG. 9 depicts a multi-segmented rod

In another embodiment, depicted in FIG. 8, an arm (118) extends from housing (104) of translation corrective mechanism (100). In this embodiment, clip member (106) is positioned at the end of arm (118). As shown, arm (118) may be bent in a variety of directions, or otherwise extend in any dimension to any suitable degree or orientation. Suitable numbers and orientations of bends in arm (118) will be apparent to those of ordinary skill in the art. It will be appreciated that a bent arm (118) may reduce the likelihood or effects of crowding of components or other structural interference during use of apparatus (10). A bent arm (118) may also increase the ease of use of apparatus (10). Alternatively, arm (118) may be substantially straight or curved. In yet another embodiment, arm (118) is adjustable. Still other variations for arm (118) will be apparent to those of ordinary skill in the art.

It will be appreciated that a variety of alternative configurations for the translation corrective mechanism (100), including but not limited to alternatives to the clip member (106), may be used.

As discussed above, the housing (82) of the facet unlocking mechanism (80) has a feature (90) configured to receive the translation screw member (108) of the translation corrective mechanism (100). The translation screw member (108) may thus impart translational forces to the facet unlocking mechanism (80). To the extent that the translation screw member (108) rotates during such translational force transfer, the feature (90) of the housing (82) may be configured such that the rotation of the translation screw member (108) does not cause or urge corresponding rotation of the facet unlocking mechanism (80). For instance, the feature (90) of the housing (82) may comprise a bushing and/or bearing assembly to absorb rotation of the translation screw member. Alternatively, the distal end of the translation screw member (108) may comprise a cap (112) or other component which is permitted to rotate freely relative to the translation screw member (108). In this embodiment, the cap (112) or other component engages with the feature (90) of the housing (82), such that no rotation is imparted to the housing (82). In one embodiment, a cap (112) includes a circumferential recess (114) which is configured to engage with an annular protrusion (116) within feature (90). Still other structures and techniques for preventing communication of rotation from the translation screw member (108) to the housing (82) of the facet unlocking mechanism (82) will be apparent to those of ordinary skill in the art. Alternatively, the translation screw member (108) may not rotate during translation at all.

The internal rods (130 or 150) of the present example are configured such that they are initially flexible, yet may be selectively made substantially rigid. The internal rods (130 or 150) each have a length that is greater than or substantially equal to the distance between the uppermost vertebra (202A) and lowermost vertebra (202B) of the affected vertebrae (200), as will be described in greater detail below. Alternatively, any other suitable length may be used. In addition, each of the internal rods (130 or 150) of the present example is dimensioned to engage with the "U"-shaped portion (24) of a cannulated screw (20), as discussed above and as will be described in greater detail below. As will be appreciated, internal rods (130 or 150) of the present example are operable to maintain an alignment of affected vertebrae (202) obtained using the facet unlocking mechanisms (80) and the translational corrective mechanisms (100), though rods (130 or 150) may serve a variety of alternative purposes.

Figure 10:
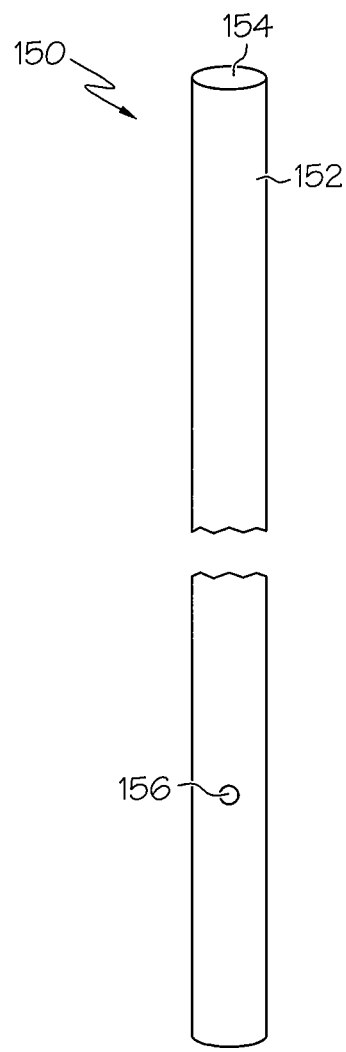
FIG. 10 depicts an internal rod.

In one embodiment, the internal rod (130) comprises a multi-segmented rod (130), such as the type commonly referred to as a "Barney Nail." A partial view of a multi-segmented rod is shown in FIG. 10. When the multi-segmented rod (130) is in a flexible state, a gap (132) is between each segment (134), which permits some movement of each segment (134) relative to adjacent segments (134). However, the segments (134) are interlocking, such that the segments (134) form a unit. In addition or in the alternative, an internal member is positioned coaxially within the segments (134), and is configured to prevent the segments (134) from falling apart. The multi-segmented rod (130) comprises a feature that permits a user to selectively make the multi-segmented rod (130) rigid. For instance, the multi-segmented rod (130) may have a screw (136) that, upon sufficient turning of the screw (136), the previously flexible multi-segmented rod (130) is made rigid. Other embodiments of a multi-segmented rod (130) suitable for use as an internal rod, and suitable substitutes for the same, will be apparent to those of ordinary skill in the art.

In another embodiment, an example of which is depicted in FIG. 10, the internal rod (150) comprises a cylindrical sleeve (152) and "liquid glass" (154) such as that owned by Medtronic, Inc. of Minneapolis, Minn. The cylindrical sleeve (152) is substantially flexible and is open at both ends. The cylindrical sleeve also has an opening (156) in its sidewall, through which the liquid glass (154) may be injected. The cylindrical sleeve (152) and liquid glass (154) are configured such that the liquid glass (154) will take the shape of the interior of the cylindrical sleeve (152), and will harden thereafter. Accordingly, the cylindrical sleeve (152) provides a mold for the liquid glass (154). After the liquid glass (154) hardens, the cylindrical sleeve (152) remains surrounding the hardened liquid glass (154). The combination of hardened liquid glass (154) and sleeve (152) forms rod (150). Of course, any other hardening liquid materials may be used to fill the cylindrical sleeve (152). Similarly, any alternative to the cylindrical sleeve (152) may be used. Still other variations of rod (150) will be apparent to those of ordinary skill in the art.

It will be appreciated that the foregoing examples of internal rods (130, 150) are merely exemplary, and that a variety alternative internal rods may be used. Similarly, suitable alternative structures other than internal rods (130, 150) may be used.

Figure 11:
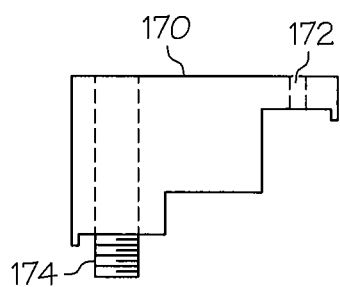
FIG. 11 depicts a side view of a clamping member.
Figure 12:
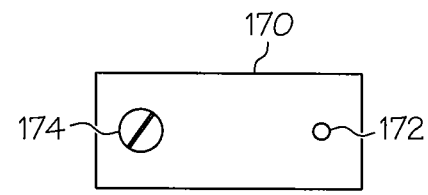
FIG. 12 depicts a top view of the clamping member of FIG. 11.
Figure 13:
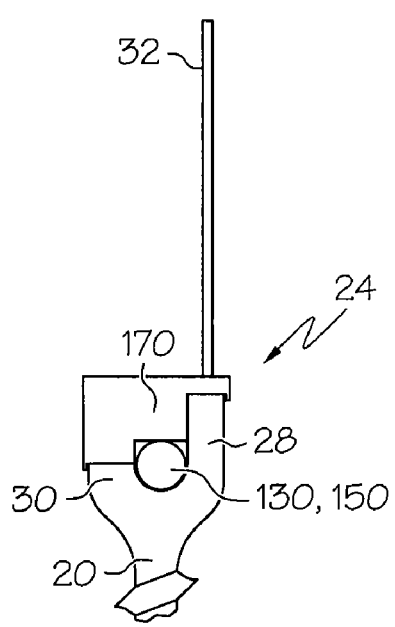
FIG. 13 depicts the clamping member of FIG. 11 engaged with the cannulated screw of FIG. 2.

As shown in FIGS. 11-13, the clamping members (170) of the present example are configured to engage with the cannulated screws (20) and the internal rods (130 or 150). Each clamping member (170) has an opening (172) through which a leading post (32) of a cannulated screw (20) may pass. The clamping members (170) are configured such that, when an internal rod (130 or 150) is positioned within the "U"-shaped portion (24) of a cannulated screw (20), the clamping member (170) may be slid down the leading post (32) of that cannulated screw (20) into position over the internal rod (130 or 150), such as in the configuration depicted in FIG. 13. Upon being positioned over the internal rod (130 or 150), the clamping member (170) may be secured to the cannulated screw (20), and optionally the internal rod (130 or 150), thereby securing the internal rod (130 or 150) to the "U"-shaped portion (24) of the cannulated screw (20) as will be described below. Of course, any other suitable component or variation of the clamping member (170) may be used to secure an internal rod (130 or 150) in place.

Any suitable material or combination of materials may be used to construct the above components. In one embodiment, all of the components that are located at least partially internal to the patient are made from a biocompatible material. In another embodiment, all of the components that will be left inside the patient are MRI compatible. In another embodiment, at least a majority of the components are made of titanium. Other suitable materials will be apparent to those of ordinary skill in the art.

While various functions and structural features of exemplary components of the present apparatus have been described above, variations of, modifications of, supplements to, and substitutes for the same will be apparent to those of ordinary skill in the art, particularly in view of the following description of exemplary uses for the present apparatus.

The apparatus (10) of the present example may be used to correct deformities of the spine, such as those mentioned above by way of example only. It will be appreciated, however, that the apparatus (10) may also be used to correct other types of deformities. The apparatus (10) may be used and installed in a minimally invasive manner. Alternatively, the apparatus (10) may be used and installed in an open procedure. In the present example, the apparatus (10) is used and installed in a minimally invasive fashion from the posterior side of the patient. While the apparatus (10) will be described below in the context of this exemplary use, it will be appreciated that the apparatus (10) may be used in any other suitable way. Various steps of several of many ways in which the apparatus (10) may be used are illustrated in FIGS. 16-23.

A preliminary step of the exemplary use of the apparatus (10) includes determining which vertebrae (200) are affected by the deformity and/or which vertebrae (200) the apparatus (10) will be engaged with, which are referred to herein as the affected vertebrae (202). In the present example, the apparatus (10) is used to correct deformity in the thoracic vertebrae (200). However, the apparatus (10) may additionally or alternatively be used with lumbar or cervical vertebrae. In addition, while the apparatus (10) is engaged with seven vertebrae (200) in the present example, it will be appreciated that the apparatus (10) may be engaged with any number of vertebrae. In present example, the affected vertebrae (202) include an uppermost vertebra (202A) and a lowermost vertebra (202B). The distance between the uppermost vertebra (202A) and the lowermost vertebra (202B) may, but need not, influence dimensions of and/or adjustments made to components of the present apparatus (10).

A pair of the screw guide wires (12) are inserted in each affected vertebra (202), such that each screw guide wire (12) of the pair is positioned in a respective pedicle (204) of the affected vertebra (202). Prior to such insertion, a small incision may be made in the skin above each portion of the affected vertebra (202) in which each screw guide wire (12) is to be inserted. In other words, in the present example, a pair of small incisions will be located above each affected vertebra (202), each incision being associated with a screw guide wire (12) insertion point (and, hence, cannulated screw (20) insertion point) for each pedicle (204) of an affected vertebra (202).

Various techniques may be used to facilitate and/or confirm proper placement of the screw guide wires (12), such as the use of X-ray or CAT scan and the like. For instance, a first X-ray may be taken of the affected vertebrae (202) prior to insertion of the screw guide wires (12) to determine the location and orientation of the pedicles (204) for the affected vertebrae (202); and a second X-ray may be taken after insertion of the screw guide wires (12) to confirm proper placement of the screw guide wires (12). In addition, after the screw guide wires (12) have been inserted, an electrical current may be applied to the guide wires (12) to detect interference of the guide wires (12) with the nervous system. Still other techniques for facilitating and/or confirming suitable placement of the screw guide wires (12) will be apparent to those of ordinary skill in the art.

With the screw guide wires (12) being properly positioned and installed, a cannulated drill bit may be positioned around each guide wire (12) (successively) and rotated to create or widen an opening in the pedicle (204) about the guide wire (12). Such drilling or reaming may facilitate subsequent insertion of cannulated screws (20), particularly where the cannulated screws (20) are not self-tapping.

Next, to facilitate spinal fusion, a facet arthrodesis may be performed. To accomplish this, a burr may be rotated at a high-speed to burr out each facet of the affected vertebrae (202). A bone enhancing material (BEM) may then be added to the facets. The BEM may comprise a bone morphogenic protein (BMP), such as BMP2 or BMP7 by way of example only. Other suitable BEMs and BMPs, as well as alternatives thereto, will be apparent to those of ordinary skill in the art.

Figure 16:
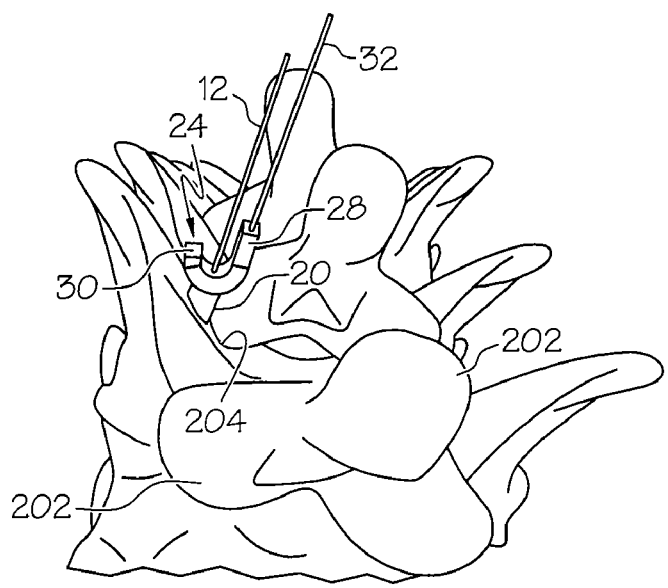
FIG. 16 depicts the cannulated screw of FIG. 2 inserted into a vertebra.

A cannulated screw (20) is then inserted percutaneously along each guide wire (12), such that a cannulated screw (20) is installed in each pedicle (204) of the affected vertebrae (202). Accordingly, in the present example, each affected vertebra (202) will have a pair of cannulated screws (20) inserted therein. The first and second arms (28, 30) of each cannulated screw (20) are oriented vertically (e.g., parallel to the axis of the patient's body). FIG. 16 depicts a cannulated screw (20) inserted along a guide wire (12) in an affected vertebra (202) in an exemplary fashion. With each cannulated screw (20) properly positioned according to the present example, the entirety of the "U"-shaped portion (24) of the cannulated screws (20) will be located below skin level, such that only the leading posts (32) extend beyond the outermost level of the skin adjacent the patient's spine. The screw guide wires (12) may be removed.

At this point, with a pair of cannulated screws (20) inserted in each affected vertebra (202), the uppermost vertebra (202A) and the lowermost vertebra (202B) should be substantially aligned vertically. The slotted external rod (40) is then placed in engagement with the uppermost vertebra (202A) and the lowermost vertebra (202B) on the concave side of the curve defined by the affected vertebrae (200). This is accomplished by inserting the leading posts (32) extending from this side of the uppermost vertebra (202A) and lowermost vertebra (202B) through the elongate slot (42) in the slotted external rod (40). The slotted external rod (40) will thus provide a reference for the remaining affected vertebrae (200), indicating a translational position that corresponding portions of the affected vertebrae (200) should reach in order to straighten the spine and therefore correct the translational deformity of the spine.

Figure 17:
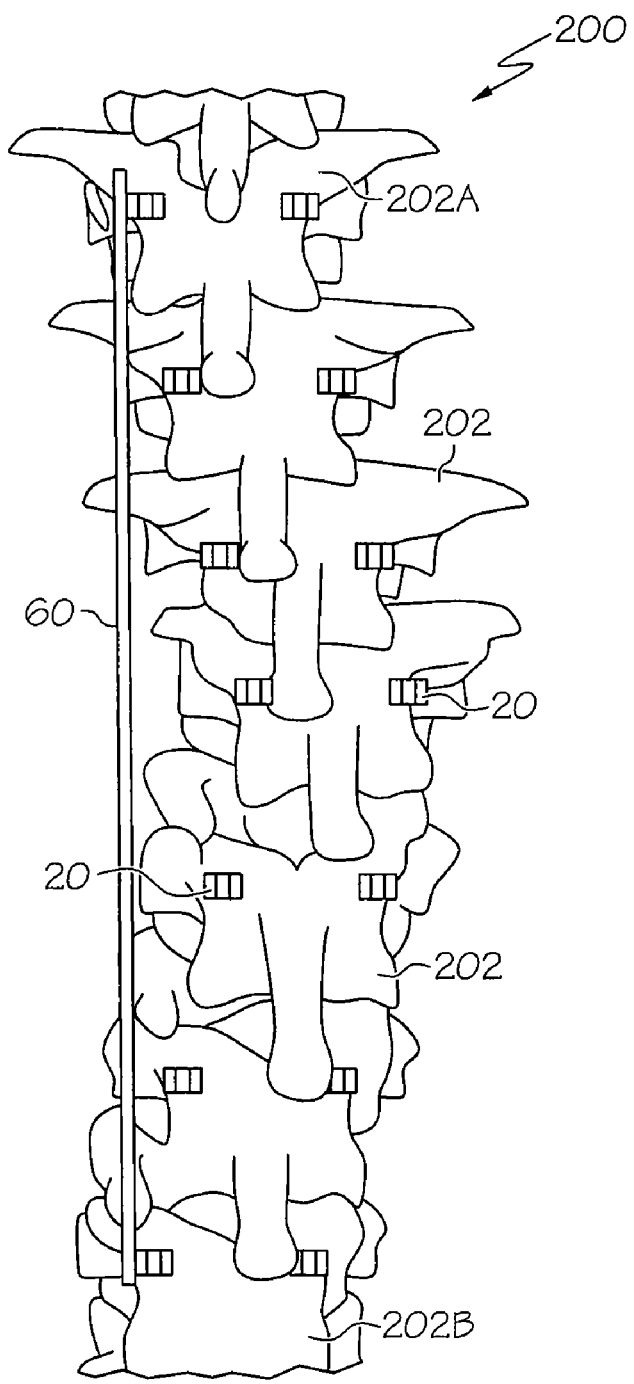
FIG. 17 depicts a plurality of cannulated screws inserted into vertebrae of a spinal column.

In a manner similar to that described above with respect to slotted external rod (40), clipping external rod (60) may be engaged with the uppermost vertebra (202A) and lowermost vertebra (202B). A schematic view of such engagement is shown in FIG. 17. It will be appreciated, however, that rods (40, 60) are merely exemplary, and that any suitable alternative structures may be engaged with the uppermost vertebra (202A) and lowermost vertebra (202B).

It will also be appreciated that, during the translational straightening of the spine, the longitudinal distance between the uppermost vertebra (202A) and lowermost vertebra (202B) may increase. By permitting axial movement of the leading posts (32) engaged therewith, the elongate slot (42) of the slotted external rod (40) may permit such extension. Similarly, longitudinal mobility of clipping members (62) along clipping external rod (60) may permit axial movement of leading posts (32) engaged therewith.

In an alternate embodiment, a second slotted external rod (40) is positioned into engagement with the other leading posts (32) of the uppermost vertebra (202A) and the lowermost vertebra (202B) (i.e., the leading posts (32) on the convex side of the curve defined by the affected vertebrae (200)). Of course, this step, along with other steps described herein, is merely optional.

Figure 18:
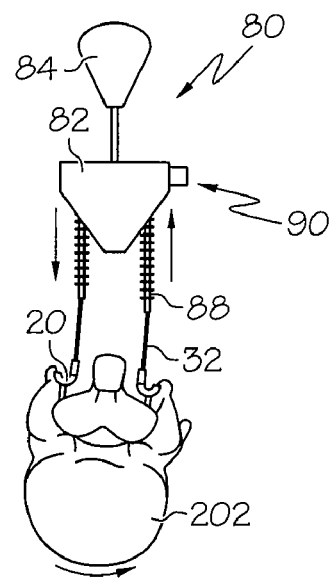
FIG. 18 depicts the facet unlocking mechanism of FIG. 6 engaged with cannulated screws inserted in a vertebra.
Figure 19:
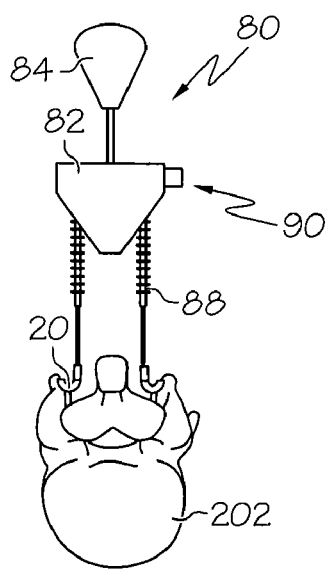
FIG. 19 depicts the facet unlocking mechanism, cannulated screws, and vertebra of FIG. 18 after the vertebra has been rotated.

Next, a facet unlocking mechanism (80) is secured to each effected vertebra (200). This is accomplished for a given affected vertebra (202) by securing each rack end (96) to a respective leading post (32) extending from the vertebra (202). This is repeated until a facet unlocking mechanism (80) has been secured to each affected vertebra (202). Exemplary engagement between a facet unlocking mechanism (80) and leading posts (32) is depicted in FIGS. 18-19.

Figure 21:
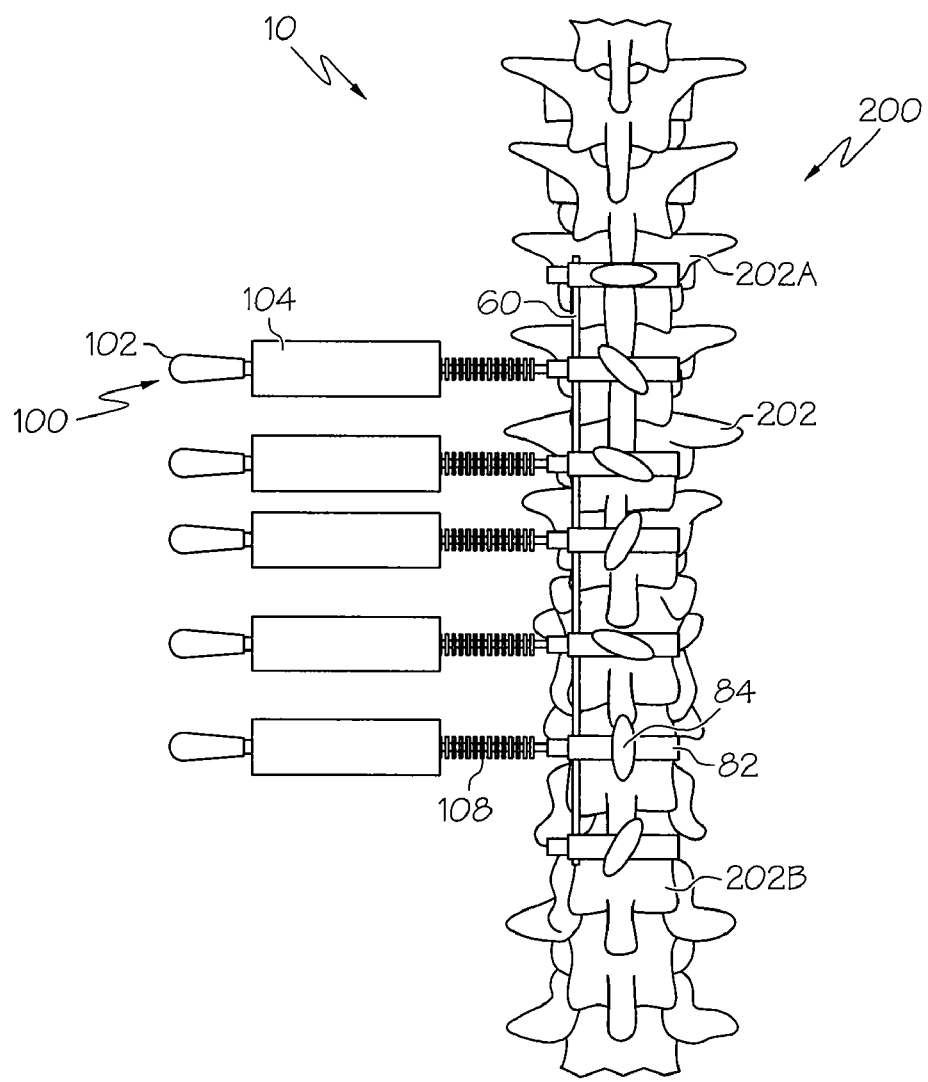
FIG. 21 depicts the plurality translation corrective mechanisms engaged with facet unlocking mechanisms engaged with cannulated screws inserted in vertebrae of a spinal column of FIG. 20 after the vertebrae have been aligned.

A translation corrective mechanism (100) is secured to each facet unlocking mechanism (80). This is accomplished by engaging a translation screw member (108) of a given translation corrective mechanism (100) with the complimentary feature (90) on the housing (82) of a given facet unlocking mechanism (80), then repeating this until each facet unlocking mechanism (80) has a translation corrective mechanism (100) secured thereto. Of course, this may be done before or during the act of securing the facet unlocking mechanisms (80) to the affected vertebrae (200). Exemplary engagement of translation corrective mechanisms (100) with facet unlocking mechanisms (80) is shown in FIGS. 21-21. It will be appreciated, however, that variations may be employed where translation corrective mechanisms (100) are not engaged with facet unlocking mechanisms (80). For instance, translation corrective mechanisms (100) and facet unlocking mechanisms (80) may be secured and/or operable independently of each other.

In the present example, each translation corrective mechanism (100) is then secured to the slotted external rod (40). This is accomplished by clipping the clip member (106) for each translation corrective mechanism (100) to the slotted external rod (40). Of course, this may be done before or during the act of securing the translation corrective mechanisms (100) to the facet unlocking mechanisms (80).

At this point in the present example, all of the facet unlocking mechanisms (80) will be engaged with respective translation corrective mechanisms (100). All of the translation corrective mechanisms (100) will be secured to the slotted external rod (40), which will itself be engaged with leading posts (32) extending from the uppermost vertebra (202A) and lowermost vertebra (202B).

Next, the knob (84) on each facet unlocking mechanism (80) is turned to unlock the facets of the affected vertebrae (200). As discussed above, this rotation of each knob (84) will effect simultaneous pushing and pulling on respective leading posts (32), thereby pushing and pulling on opposite pedicles (204) of a respective vertebra (202). It will be appreciated that such pushing and pulling will rotate the respective vertebra (202) to unlock the facets and correct rotational deformity. FIGS. 18-19 depict a series view of such rotation of an affected vertebra (202). This process will be repeated for each of the affected vertebrae (202), as necessary or desired. The relative position of the leading posts (32) extending from a given vertebra (202) may be observed to provide visual feedback indicating the rotational orientation of the vertebra (202). In other words, where the ends of the leading posts (32) extending from a vertebra (202) are at the same horizontal level, such may indicate that that vertebra (202) is rotationally aligned, and therefore that the facet has been unlocked. Other techniques for determining proper rotational alignment or orientation, and hence, the unlocking of the facets, will be apparent to those of ordinary skill in the art.

Figure 20:
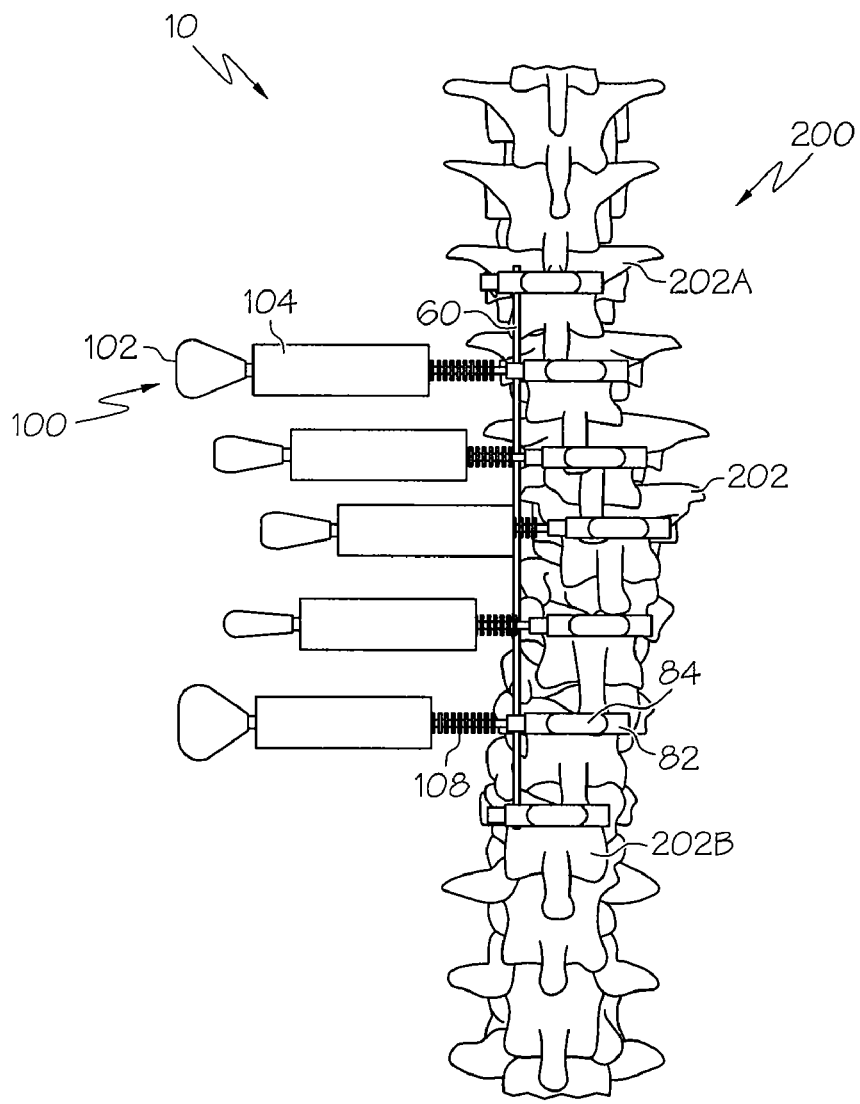
FIG. 20 depicts a plurality translation corrective mechanisms engaged with facet unlocking mechanisms engaged with cannulated screws inserted in vertebrae of a spinal column.

When all of the facets have been unlocked using the facet unlocking mechanisms (80), the affected vertebrae (200) are brought into axial alignment using the translation corrective mechanisms (100). In particular, the knob (102) is rotated on each translation corrective mechanism (100) to push or pull (via the translation screw member (108)) on the facet unlocking mechanism (80) with which each translation corrective mechanism (100) is engaged. This translational movement will be communicated to each of the affected vertebrae (200) through the corresponding facet unlocking mechanism (80) by virtue of engagement between the rack ends (92) and the leading posts (32). FIGS. 20-21 depict a series view of such translation of affected vertebra (202).

During the translation correction described above, it may be desirable to begin with the first affected vertebra (200) that is adjacent to the uppermost vertebra (202A) or the lowermost vertebra (202B), then work on each affected vertebra (200) successively toward the other of the uppermost vertebra (202A) or the lowermost vertebra (202B). It will be appreciated that, as each affected vertebra (200) is brought into alignment with the uppermost vertebra (202A) and lowermost vertebra (202B), crowding of components of the apparatus (10) may occur. For instance, during translation of a given vertebra (200), the leading post (32) nearest the slotted external rod (40) may run into the side of the slotted external rod (40) before that vertebra (200) is properly aligned, such that the slotted external rod (40) prevents that vertebra (200) from obtaining complete alignment. When this occurs, the leading post (32) with which the slotted external rod (40) is interfering may be temporarily removed, then reinserted through the slot (42) upon proper alignment of that vertebra (202). Still other techniques for addressing such component interference will be apparent to those of ordinary skill in the art. By way of example only, substituting the slotted external rod (40) with the external rod (60) having freely longitudinally sliding clips (62) may address such interference without requiring such temporary removal of the leading posts (32).

It will also be appreciated that the leading posts (32) may exert substantial stress on adjacent skin during translational correction, particularly where the curvature of the spine is very pronounced. In some situations, this stress may not need to be addressed. In others, a small, transverse incision may be made to provide a path for the leading post (32) during translational correction. Other techniques for addressing the effects of leading posts (32) on the skin during translational correction will be apparent to those of ordinary skill in the art.

Upon completion of translational correction using the translation corrective mechanisms (100), the affected vertebrae (202) should be properly aligned, and all of the leading posts (32) should define a pair of parallel columns. With respect to the leading posts (32) on what had previously been the concave side of the curve defined by the affected vertebrae (202), those leading posts (32) will be engaged with the slotted external rod (40). The other leading posts (32) (i.e. those on what had previously been the convex side of the curve defined by the affected vertebrae (200)) are then engaged with a clipping external rod (60). At this point, the slotted external rod (40) may be replaced with the other clipping external rod (60). Alternatively, each column of leading posts (32) may be engaged with a respective slotted external rod (40). Upon the securing of a rod (40 or 60) or other member to each column of leading posts (32), the facet unlocking mechanisms (80) and translation corrective mechanisms (100) may be removed.

Next, a pair of small incisions are made near the uppermost vertebra (202A) and the lowermost vertebra (202B). The incisions should correspond with the translational position of the "U"-shaped portions (24) of the cannulated screws (20) on each side of the spinal column.

A first rod guide wire (120) is then inserted through one of the above-described incisions, and is fed along the "U"-shaped portions (24) of the cannulated screws (20) on the corresponding side (e.g., the right side) of the spinal column. The inserted end of the rod guide wire (120) is then passed through the other incision on that side of the spinal column (i.e., at the other end of the column). Each end of the rod guide wire (120) will thus extend from each incision at the respective ends of that side of the spinal column. The same process is employed with the other rod guide wire (120) for the other side (e.g., the left side) of the spinal column. An X-ray or other device or technique may be used to confirm proper position for each of the rod guide wires (120). Once the rod guide wires (120) are properly positioned, an end of each guide wire (120) may be secured in place or simply held.

Figure 22:
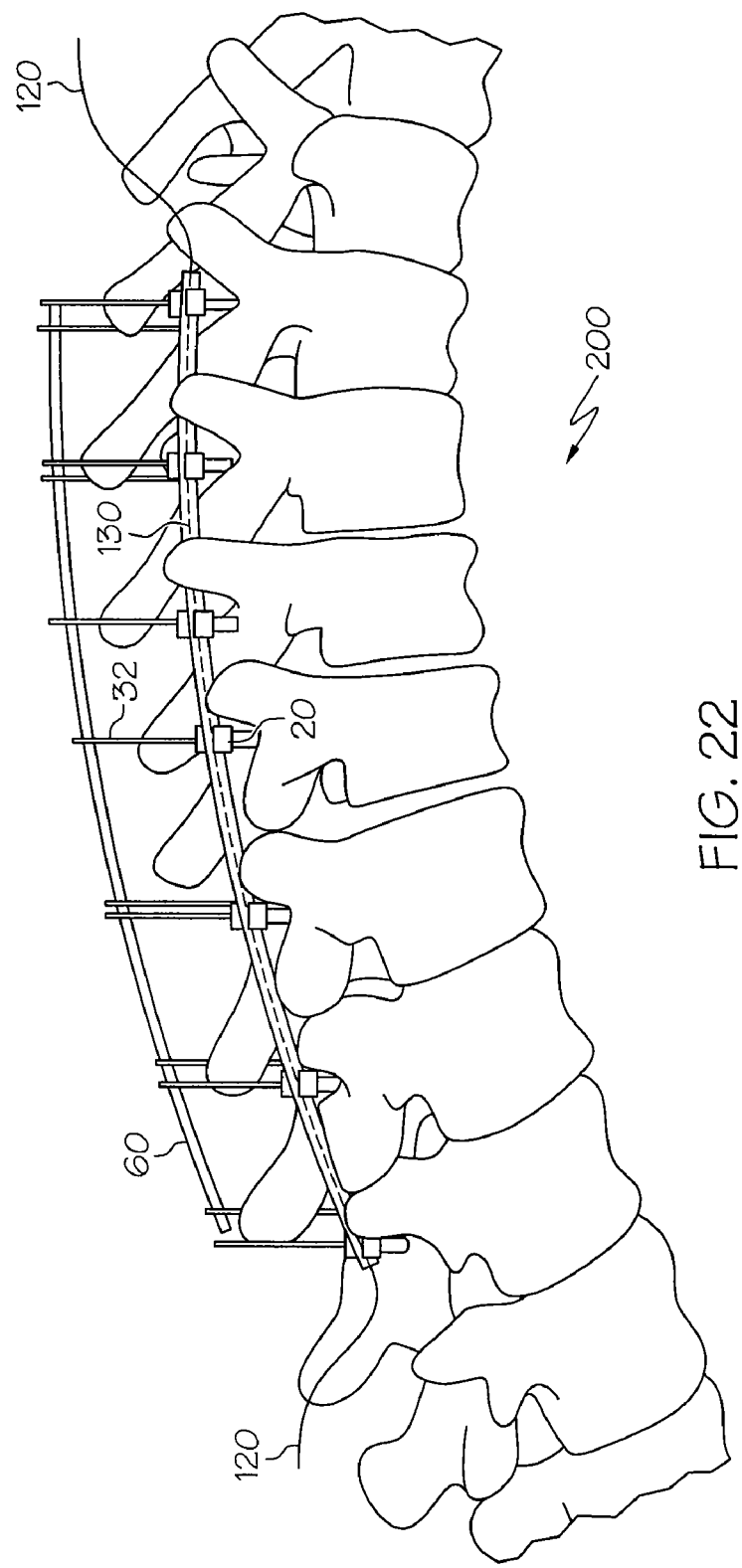
FIG. 22 depicts the multi-segmented rod of FIG. 9 engaged with cannulated screws inserted into vertebrae of a spinal column.
Figure 23:
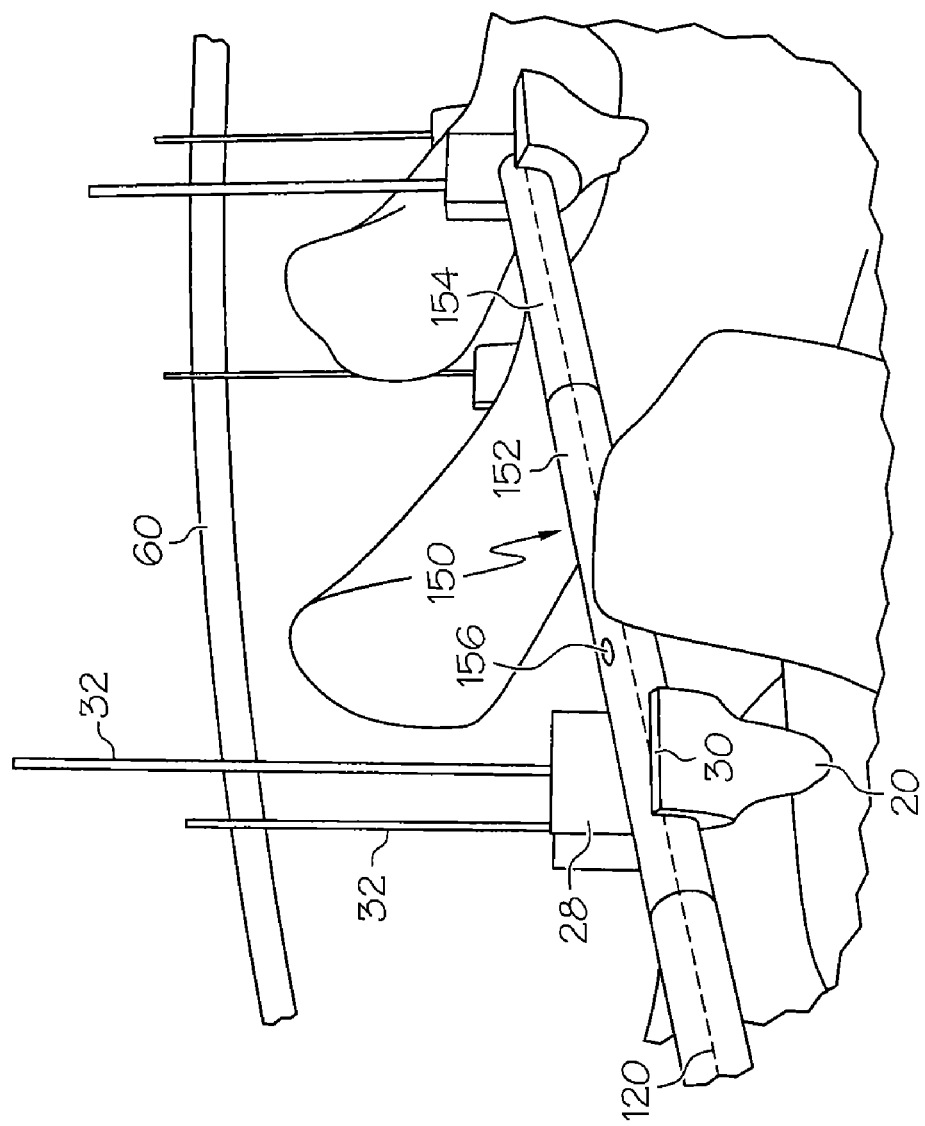
FIG. 23 depicts a cylindrical sleeve and liquid glass engaged with cannulated screws inserted into vertebrae of a spinal column.

An internal rod (130 or 150) is then percutaneously inserted through one of the incisions along one of the rod guide wires (120). The internal rod (130 or 150) is then positioned in the "U"-shaped portions (24) of the cannulated screws (20) on that side of the spinal column. Another internal rod (130 or 150) is percutaneously inserted along the other guide wire (120), and positioned in the "U"-shaped portions (24) of the cannulated screws (20) on the other side of the column.

Where the internal rod (130) comprises the multi-segmented rod (130), the multi-segmented rod (130) is inserted along the guide wire (120) while the multi-segmented (130) rod is in its flexible form. FIG. 22 shows multi-segmented rod (130) inserted along guide wire (120) in an exemplary fashion. Gaps (132) and individual segments (134) of multi-segmented rod (130) are not shown in FIG. 22.

Where the internal rod (150) comprises the cylindrical sleeve (152) and the liquid glass (154), the cylindrical sleeve (152) is first inserted along the rod guide wire (120). The liquid glass (154) is then injected into the transverse opening (156) of the cylindrical sleeve (152) to fill the cylindrical sleeve (152). The liquid glass (154) is allowed to harden. The rod guide (120) wire may be removed prior to hardening, or may be left in its place. FIG. 23 shows internal rod (150) inserted along guide wire (120) in an exemplary fashion. Portions of cylindrical sleeve (152) and liquid glass (154) are not shown in FIG. 23.

Regardless of the type of internal rod (130 or 150), when the internal rod (130 or 150) has been properly positioned in the present example, a clamping member (170) is inserted along each leading post (32) to secure the internal rod (130 or 150) to the respective cannulated screw (20). An exemplary view of a clamping member (170) engaged with an internal rod (130 or 150) and cannulated screw (20) is shown if FIG. 13. During the insertion of each clamping member (170), one of the clipping external rods (60) may interfere with the clamping member (170), such that it may be necessary to provide clearance for the clamping member (170) as it traverses the leading post (32) toward the internal rod (130 or 150). Such clearance may be provided by temporarily removing the interfering clipping external rod (60) during such traversal, while maintaining the other clipping external rod (60) in place. Alternatively, each clipping external rod (60) may comprise a feature that is operable to provide clearance of the clipping external rod (60) by the clamping member (170) without requiring complete removal of the clipping external rod (60). For instance, the interfering clipping member (62) of the clipping external rod may be rotated away from the leading post (32). Still other ways in which such interference may be addressed will be apparent to those of ordinary skill in the art.

When a given clamping member (170) has been positioned over an internal rod (130 or 150), the clamping member (170) may be secured to the cannulated screw (20), thereby securing the internal rod to the cannulated screw (20). For instance, the clamping member (170) may comprise an opening, and the second arm defining the "U"-shaped portion of the cannulated screw (20) may comprise a threaded opening, such that a screw (174) may be engaged with these openings to secure the clamping member (170) to the cannulated screw (20). In addition, the clamping member (170) and/or the internal rod (130 or 150) may comprise a feature permitting engagement between the clamping member (170) and the internal rod (130 or 150), such that movement of the internal rod (130 or 150) relative to the clamping member (170) is prohibited. For instance, the components may have complimentary surface features such as tabs and slots. Alternatively, a pair of openings may be configured to receive a screw to secure the clamping member (170) to the internal rod (130 or 150). Alternatively, relative movement between the clamping member (170) and the internal rod (130 or 150) may be prevented by friction. Still other structures and techniques for securing the internal rod (130 or 150) in place relative to the cannulated screws (20) will be apparent to those of ordinary skill in the art.

After the first internal rod (130 or 150) has been secured in place along one side of the spinal column, the second internal rod (130 or 150) is secured in place along the other side of the spinal column in a similar fashion.

At this point in the present example, the affected vertebrae (202) have been rotationally and translationally aligned, and have been secured in such alignment by the secured internal rods (130 or 150). All remaining external components of the apparatus (10) (or external portions of components) may thus be removed, including the clipping external rods (60), the leading posts (32), and the rod guide wires (120) (or external portions of the rod guide wires (120)).

After removal of the external components (or portions thereof), the incisions may be sutured. In the present example, the incisions include two small incisions for each affected vertebra (202) (one for insertion of each guide wire (12) and corresponding cannulated screw (20)), two small incisions for each rod guide wire (120), and any incisions required to accommodate translational movement of the leading posts (32) during translational correction. It will thus be appreciated that the present apparatus (10) may be used to correct spinal deformities in a minimally invasive fashion from the posterior side of the patient.

While several embodiments of the present apparatus (10) and methods of using the same have been described above, it will be appreciated that various modifications, supplements, and/or substitutes may be used. For instance, a single internal rod (130 or 150) may be used instead of two.

Figure 14:
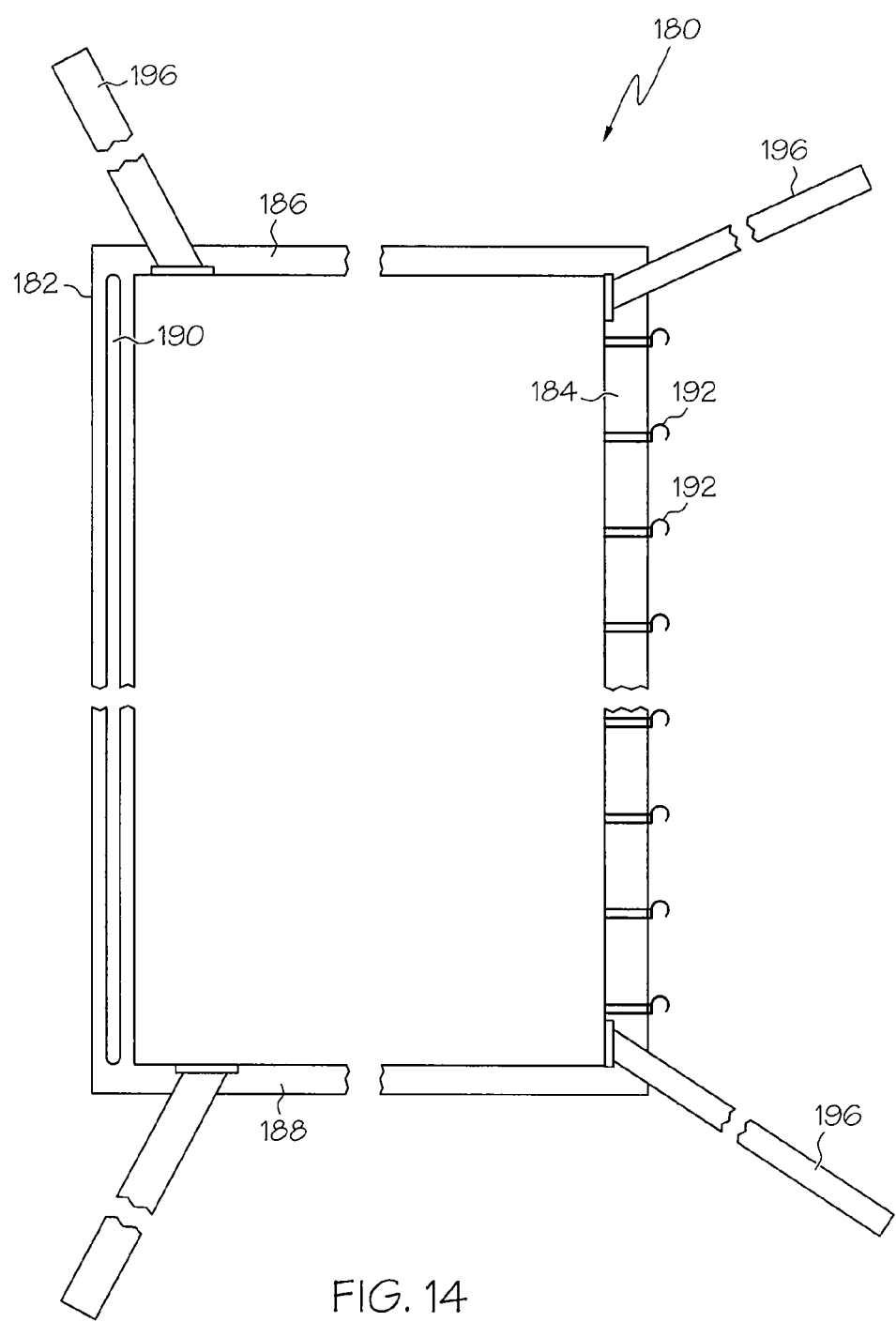
FIG. 14 depicts a frame assembly.

In another embodiment, the slotted external rod (40) is substituted with a frame assembly (180), an example of which is depicted in FIG. 14. The frame assembly (180) has a generally rectangular shape, with two long parallel members (182, 184) and two short parallel members (186, 188), which are substantially perpendicular to the two long parallel members (182, 184). One of the long members (182) has an elongate slot (190), similar to the a slot (42) of the slotted external rod (40). The other long member (184) has a plurality of swiveling hook members (192), whose longitudinal position along the long member (184) is adjustable and fixable. The slotted long member (182) is configured to receive the translation corrective mechanisms (100) in a manner similar to the slotted external rod (40). The long member (184) with hook members (192) is configured to engage with the leading posts (32). The swiveling hook members (192) act as clamps, such that they are configured to selectively secure the leading posts (32) to or adjacent to the corresponding long member (184) of the frame assembly (180). With the leading posts (32) so secured to that member (184) of the frame assembly (180), relative movement between the secured leading posts (32) and the frame assembly (180) is permitted only in the longitudinal direction. Of course, such movement may also be restricted.

The method of using the frame assembly (180) is substantially similar to the method of using the slotted external rod (40). However, by spacing the translation corrective mechanisms (100) further away from the leading posts (32), the likelihood of interference may be reduced. In addition, during translational correction, as a leading post (32) approaches the frame assembly (180), the corresponding hook member (192) may simply be swiveled away to permit the leading post (32) to engage with the corresponding side (184) of the frame assembly (180). The hook member may (192) then be swiveled back to capture and secure the leading post (32) to the frame assembly (180). Hook members (192) may include a mechanism for selectively preventing a leading post (32) from escaping a hook member (192) once the hook member (192) has been captured and secured the leading post (32). For instance, such a mechanism may comprise a latch, clasp, pin insertable into openings, a protrusion-recess combination, or any other components or features.

In addition, the frame assembly (180) may serve as a substitute for the clipping external rods (60). In such an embodiment, where a clamping member (170) is being inserted along a leading post (32) to secure an internal rod (130 or 150) to a cannulated screw (20), the corresponding hook member (192) may again be swiveled away to provide clearance.

The frame assembly (180) may further comprise one or more removable and/or adjustable support members (196). Of course, support members (196) need not be adjustable or removable. To the extent that support members (196) are adjustable, the support members (196) may be adjustable with respect to length and/or orientation. The support members (196) may rest at any suitable location on the patient's back or elsewhere. The support members (196) may provide additional stability and/or reduce stress on the leading posts (32) during facet unlocking and/or translational correction. It will be appreciated that the frame assembly (180) may have a variety of other features and functions. It will also be appreciated that frame assembly (180) need not necessarily be rectangular, and may have any other suitable configuration.

Figure 15:
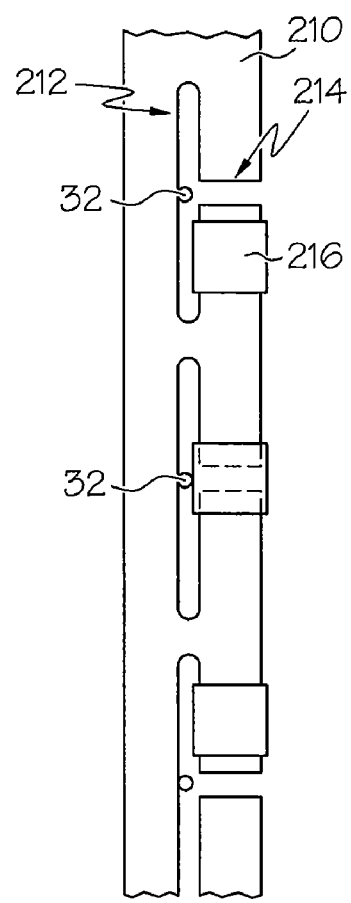
FIG. 15 depicts a partial view of an elongate member.

In yet another embodiment, an elongate member (210) includes a plurality of longitudinal slots (212) and a plurality of transverse slots (214). A partial view of an elongate member (210) is shown in FIG. 15. Each of the transverse slots (214) is in communication with a respective longitudinal slot (212). In one embodiment, each transverse slot (214) and longitudinal slot (212) is dimensioned to accommodate a leading post (32). For instance, each transverse slot (214) may be configured to permit a leading post (32) to pass into a respective longitudinal slot (212). Each transverse slot (214) may provide a gap that is sufficiently wide enough to permit access to the respective longitudinal slot (212) from a wide range of longitudinal positions (e.g., such that elongate member (210) may be used for a variety of patients having a variety of spinal lengths).

The elongate member (210) further comprises a plurality of locking members (216). Each of the locking members (216) may be moved longitudinally along elongate member (210). Each locking member (216) is positioned proximate to a respective transverse slot (214) and may be selectively moved to cover (a "covering position") and uncover (an "uncovering position") the respective transverse slot (214). The elongate member (210) may further comprise a feature that is operable to secure each locking member (216) in one or more of the covering position or the uncovering position. It will be appreciated that the elongate member (210) may be used to supplement apparatus (10) and/or may be used as a substitute for slotted external rod (40), clipping external rod (60), long member (182) and/or long member (184).

In another embodiment (not shown) of elongate member (210), the transverse slot (214) and longitudinal slot (212) are combined to form a rectangular recess in the side of elongate member (210). That is, the rectangular recess is defined by a longitudinal wall that has a length approximately equal to that of longitudinal slot (212) in the prior embodiment, and is further defined by a pair of radial walls extending perpendicularly from each end of the longitudinal wall. In this embodiment, each locking member (216) is configured such that it has a length that is greater than the longitudinal dimension of the respective rectangular recess. It will be appreciated that this embodiment may permit the capture of a leading post (32) within the rectangular recess by a locking member (216) from a wide range of longitudinal positions, thereby facilitating the use of elongate member (210) for a variety of spinal lengths. Each locking member (216) in this variation may encompass the full circumference of elongate member (210), and may comprise a slot (not shown) to provide clearance for a leading post (32) as the locking member (216) is slid into place. Still other variations of elongate member (210), including uses thereof, will be apparent to those of ordinary skill in the art.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings.

What is claimed is:

1. A system for correcting spinal deformity, comprising:
   (a) a plurality of anchor members, wherein each of the anchor members is configured to be inserted percutaneously into the spine of a patient;
   (b) a stabilizing member, wherein the stabilizing member is configured to engage at least one of the anchor members when the stabilizing member is external to the patient and when the anchor members are inserted into the spine of the patient;
(c) a translation correction mechanism, wherein the translation correction mechanism is securable relative to the stabilizing member and relative to at least one respective anchor member, wherein the translation correction mechanism is operable to move a vertebra translationally relative to the stabilizing member; and
(d) a facet unlocking mechanism, wherein the facet unlocking mechanism is securable relative to the stabilizing member and relative to at least one respective anchor member, wherein the translation correction mechanism is operable to rotate a vertebra relative to the spinal column of the patient, wherein the translation correction mechanism is engageable with the facet unlocking mechanism.

2. The system of claim 1, further comprising an internal rod, wherein the internal rod is configured to engage a portion of the plurality of anchor members, wherein the internal rod is percutaneously insertable into the patient, wherein the internal rod is configured to maintain an alignment of vertebrae obtained with at least one translation correction mechanism and at least one facet unlocking mechanism.

3. The system of claim 2, wherein the internal rod is operable to be selectively placed in a flexible mode or a rigid mode.

4. The system of claim 2, wherein the internal rod comprises a plurality of segments joined together, wherein the rod defines an axis, wherein the segments are positioned serially along the axis.

5. The system of claim 2, wherein the internal rod comprises a hardened liquid.

6. The system of claim 5, wherein the internal rod further comprises a sleeve, wherein the hardened liquid is provided within the sleeve.

7. The system of claim 2, further comprising a plurality of securing members, wherein each securing member is configured to percutaneously secure the internal rod relative to a corresponding anchor member of the plurality of anchor members.

8. The system of claim 1, wherein each of the anchor members comprises a post configured to extend externally from the patient when the anchor member is inserted into the spine of the patient.

9. The system of claim 8, wherein the facet unlocking mechanism is configured to engage a pair of posts extending from a corresponding pair of anchor members.

10. The system of claim 1, wherein each of the anchor members comprises a screw.

11. The system of claim 1, wherein the stabilizing member comprises a rod.

12. The system of claim 11, wherein the rod comprises a slot.

13. The system of claim 11, wherein the rod comprises a plurality of fastening mechanisms, wherein each of the fastening mechanisms is operable to selectively secure the rod relative to a corresponding anchor member.

14. The system of claim 1, wherein the stabilizing member comprises a frame assembly.

15. The system of claim 1, wherein the translation correction mechanism comprises a shaft and a housing, wherein the shaft and housing define an axis, wherein the shaft is longitudinally movable along the axis.

16. The system of claim 1, wherein the facet unlocking mechanism comprises a rack and pinion.

17. The system of claim 1, wherein the stabilizing member is externally removable relative to the patient.

18. A system for correcting spinal deformity, comprising:
(a) a plurality of anchor members, wherein each of the anchor members is configured to be inserted percutaneously into the spine of a patient;
(b) an external stabilizing member, wherein the external stabilizing member is configured to engage at least one of the anchor members when the external stabilizing member is external to the patient and when the anchor members are inserted into the spine of the patient;
(c) a translation correction mechanism, wherein the translation correction mechanism is securable relative to the external stabilizing member, wherein the translation correction mechanism is operable to move a vertebra translationally relative to the external stabilizing member via at least one corresponding anchor member;
(d) a facet unlocking mechanism, wherein the facet unlocking mechanism is securable relative to the external stabilizing member, wherein the translation correction mechanism is operable to rotate a vertebra relative to the spinal column of the patient via at least one corresponding anchor member, wherein the facet unlocking mechanism comprises a rack and pinion; and
(e) an internal stabilizing member, wherein the internal stabilizing member is engagable with at least a portion of the plurality of anchor members, wherein the internal stabilizing member is configured to be percutaneously introduced to at least a portion of the plurality of anchor members.

19. A system for correcting spinal deformity, comprising:
(a) a plurality of anchors, wherein the anchors are percutaneously insertable into the spine of a patient;
(b) means for rotating vertebrae of the patient via at least a portion of the plurality of anchors, wherein the means for rotating vertebrae of the patient is manipulable external to the patient, wherein the means for rotating vertebrae of the patient is operable to transfer opposing axial forces to the plurality of anchors;
(c) means for translationally moving vertebrae of the patient via at least a portion of the plurality of anchors, wherein the means for translationally moving vertebrae is manipulable external to the patient; and
(d) means for maintaining an alignment of vertebrae obtained using the means for rotating vertebrae and the means for translationally moving vertebrae, wherein the means for maintaining an alignment is percutaneously insertable into the patient.

* * * * *